US 7,301,639 B1

(12) United States Patent
Kebabian et al.

(10) Patent No.: US 7,301,639 B1
(45) Date of Patent: Nov. 27, 2007

(54) SYSTEM AND METHOD FOR TRACE SPECIES DETECTION USING CAVITY ATTENUATED PHASE SHIFT SPECTROSCOPY WITH AN INCOHERENT LIGHT SOURCE

(75) Inventors: Paul L. Kebabian, Acton, MA (US); Andrew Freedman, Chelmsford, MA (US)

(73) Assignee: Aerodyne Research, Inc., Billerica, MA (US)

( * ) Notice: Subject to any disclaimer, the term of this patent is extended or adjusted under 35 U.S.C. 154(b) by 447 days.

(21) Appl. No.: 10/987,637

(22) Filed: Nov. 12, 2004

(51) Int. Cl.
*G01N 21/00* (2006.01)

(52) U.S. Cl. .................................................. 356/437

(58) Field of Classification Search ......... 356/436–440
See application file for complete search history.

(56) References Cited

U.S. PATENT DOCUMENTS 5,528,040 A * 6/1996 Lehmann .................... 250/343
5,793,545 A * 8/1998 Monfre et al. .............. 359/891

OTHER PUBLICATIONS

Ball et al.; "Broadband cavity enhanced absoprtion spectroscopy using light emitting diodes";Oct. 5, 2004; Chemical Physics Letters 398 (2004) 68-74.*
Engeln et al., "Phase shift cavity ring down absorption spectroscopy," Chemical Physics Letters, Jun. 14, 1996, pp. 105-109, 262 (1996), Elsevier Science B.V.
Scherer et al., "Cavity Ringdown Laser Absorption Spectrosopy: History, Development, and Application to Pulsed Molecular Beams," Chemical Review, 1997, pp. 25-51, 97 (1997), American Chemical Society.
Hamers et al., "Fourier transforms phase shift cavity ring down spectroscopy," Chemical Physics Letters, Sep. 9, 2002, pp. 237-243, 365 (2002), Elsevier Science B.V.
Fiedler et al., "Incoherent broad-band cavity-enhanced absorption spectroscopy," Chemical Physics Letters, Jan. 16, 2003, pp. 284-294, 371 (2003), Elsevier Science B.V.
Steven S. Brown, "Absorption Spectroscopy in High-Finesse Cavities for Atmospheric Studies," Chemical Review, Mar. 6, 2003, pp. 5219-5238, 103 (2003), American Chemical Society.
Ball et al., "Broad-Band Cavity Ring-Down Spectroscopy," Chemical Review, Apr. 7, 2003, pp. 5239-5262, 103 (2003), American Chemical Society.

* cited by examiner

*Primary Examiner*—Gregory J. Toatley, Jr.
*Assistant Examiner*—Amanda H Merlino
(74) *Attorney, Agent, or Firm*—Cesari and McKenna LLP

(57) ABSTRACT

This invention provides a system and method that enables the use of incoherent light sources, such as light emitting diodes, to provide for the detection of gaseous species which exhibit broadband absorption features (e.g., nitrogen dioxide and the halogen gases). The light emitting diode (LED) is an ideal light source for such an arrangement in that it can be modulated at high frequencies (allowing for omission of external modulation equipment) and provides sufficient illumination within a reasonably narrow wavelength band as compared to, for instance, an incandescent light source. A further advantage of a LED as a light source compared to alternatives such as a gas discharge or arc lamp is that the light output of the LED is highly stable, limited by the stability of the current source used to drive it. Use of a confocal or near-confocal resonant optical cavity maximizes coupling of the light source to the cavity.

25 Claims, 4 Drawing Sheets

SYSTEM AND METHOD FOR TRACE SPECIES DETECTION USING CAVITY ATTENUATED PHASE SHIFT SPECTROSCOPY WITH AN INCOHERENT LIGHT SOURCE

STATEMENT REGARDING FEDERALLY SUPPORTED RESEARCH OR DEVELOPMENT

This invention was made with government support under Small Business Innovation Research award: DE-FG02-03ER83598. The government has certain rights in this invention.

BACKGROUND OF THE INVENTION

1. Field of the Invention

This invention relates to detection of trace chemical species in a gaseous sample and more particularly to detection of species using phase shift cavity ring down absorption spectroscopy.

2. Background Information

Nitrogen oxide species ($NO_x$), in general, are important in determining the photochemistry of the earth's atmosphere, controlling the formation of tropospheric ozone, affecting the concentration of the hydroxyl (—OH) radical and contributing to acidic precipitation. Nitrogen dioxide ($NO_2$), specifically, is formed by reaction of NO, a primary air pollutant produced during fossil fuel combustion from both stationary and mobile sources, with ozone and is converted back to NO by photolysis on a time scale of a few seconds to several minutes. In urban areas, high nitrogen dioxide concentrations can produce significant health effects on human populations, lead to photochemical "smog" formation, and decrease visibility due to secondary aerosol formation. In the U.S., nitrogen dioxide is regulated by a national ambient air quality standard (NAAQS) under the 1970 Clean Air Act. Detection and measurement of $NO_2$ and other chemical species is quite important in monitoring and controlling such pollution. In addition, detection of nitrogen-based compounds and other species is becoming more desirable in the search for controlled substances, chemical poisons and explosive materials in transportation and public areas.

Currently, the most widely used technique for the measurement of nitrogen dioxide involves reducing it to NO using a heated molybdenum catalyst, followed by detecting the chemiluminescent reaction of NO with ozone. This technique is capable of achieving sensitivities in the sub-part-per-billion range and has historically remained the system-of-choice in air pollution and other atmospheric studies because of its reliability and comparatively low cost. However, this technique has been shown to be prone to interference from other nitrogen/oxygen-containing atmospheric trace species, such as peroxy nitrates and alkyl nitrates. As a result, the "measured" concentration of nitrogen dioxide can be considerably higher than the actual concentration.

It has been recognized that laser-based absorption and induced fluorescence techniques provide sufficient sensitivity and specificity to alleviate the problem of interfering species. Field-ready systems employing these techniques are, however, quite expensive and tend to require highly competent personnel to operate them. For example, two such techniques, cavity attenuated phase shift spectroscopy (CAPS) and cavity ringdown laser absorption spectroscopy (CRDS), employ a coherent light source, such as a laser to detect ambient gases within a test cavity defined by two or more mirrors that minimize optical loss. A detector is placed adjacent to one of the mirrors. Given the low loss, highly-reflective characteristic of the cavity, injected photons make many passes through the space of the cavity before slowly "leaking out" and traveling to the detector. For a given mirror reflectivity R the average number of round trips n made by a photon within the 2-mirror cavity is expressed as:

$$N = R^2/(1-R^2).$$

Note that for R=0.9998 (readily obtainable now because of the development of the cavity ringdown technique), a cavity of 0.5 meter in length produces an effective path length of over 1 km. Referring to the graph 100 in FIG. 1, if a sine wave modulated continuous light source is coupled into the optical cavity, the resulting waveform 102 reaching the detector (shown as $\gamma_1$ in FIG. 1) will be shifted in phase from the original waveform 104, a change which is readily measured with high accuracy using a lock-in amplifier. A square wave modulated light source may also be employed with similar results. Note that in this example, the modulation frequency is generally chosen so that $\gamma_1 = 45°$. The presence of a gaseous species within the cavity adds another loss mechanism that competes with leakage of light through the opposing mirrors resulting in the curve 106. This additional loss term contributes to a change in the magnitude of the detected phase angle ($\gamma_2$) of the modulated light, which allows one to detect the species of choice. In other words, the greater the absorbance of the gas in the sample cell, the faster the energy stored in the cavity decays, causing the measured phase shift, $\Delta\gamma$ (defined as $\gamma_1 - \gamma_2$) to increase. The nominal change in phase shift, ignoring the fact that the mirror reflectivity, R and gas absorption, A, vary as a function of wavelength, can be expressed as:

$$\Delta\gamma = 45° - \arctan[((1-R)^2(1-A)^2)/(1-R^2(1-A)^2)]$$

For convenience, the phase shift has been defined as a positive for increased light absorption.

More particularly, systems based on either phase shift cavity ring down absorption spectroscopy and time decay cavity ringdown spectroscopy have typically coupled coherent light sources, i.e., lasers, with the resonant cavity so as to excite only a few modes of the cavity. To do so, the cavities have been designed to act similarly to laser cavities in which the radius of curvature of the cavity mirrors is long compared to the cavity length. This arrangement necessarily leads to low optical throughput when a spatially incoherent light source is employed. Furthermore, the use of coherent light sources necessarily entails complex apparatus in order to maintain the laser frequency at the resonant frequency of the cavity.

One particular problem with the use of a coherent light source is that all axial and transverse modes of the resonant optical cavity may not be equally excited. If the gas absorption shows any dependence on optical frequency at the scale of the free spectral range of the cavity, changes in cavity length on the order of a fraction of a wavelength of the light used cause measurable changes in the phase shift at constant absorber concentration. In general, it is difficult to maintain a laser frequency at the resonant frequency of the cavity, particularly where slight variations in cavity length may occur due to external forces and temperature variations. Overall, the deficiencies of a coherent light source-based cavity add significantly to the expense and complexity in the setup and maintenance of the apparatus Resonant optical cavities designed to employ incoherent light sources have been designed. However, these designs are also limited in function and employ costly components. In one arrangement the output of a CW xenon arc lamp is modulated using an external photoelastic modulator—as this lamp cannot be effectively modulated by simply clocking the driving current input. The wavelength of light allowed to enter the resonant cavity is then selected with a Michelson interferometer posed between the lamp and cavity. The light leaking from the cavity is detected using a lock-in amplifier. A useable spectrum that is indicative of the species is obtained by incrementally step-scanning the interferometer's mirror. Clearly, this incoherent light technique involves sensitive and costly equipment that must be set up and maintained by a skilled technician.

It is desirable to provide an improved technique for detecting $NO_2$ and other chemical species that maintains the advantages of quick detection time, species selectivity and concentration sensitivity of coherent-light-source CAPS without the limitations imposed by the use of a laser or other coherent light source or complex interferometer-based, incoherent-light driven cavity.

SUMMARY OF THE INVENTION

The invention overcomes the disadvantages of the prior art by enabling the use of incoherent light sources, such as light emitting diodes, to provide for the detection of gaseous species which exhibit broadband absorption features (e.g., nitrogen dioxide and the halogen gases). The light emitting diode (LED) is an ideal light source for such an arrangement in that it can be modulated at high frequencies (allowing for omission of external modulation equipment) and provides sufficient illumination within a reasonably narrow wavelength band as compared to, for instance, an incandescent light source. A further advantage of a LED as a light source compared to alternatives such as a gas discharge or arc lamp is that the light output of the LED is highly stable, limited by the stability of the current source used to drive it. Use of a confocal or near-confocal resonant optical cavity maximizes coupling of the light source to the cavity.

In an illustrative embodiment, the modulated LED light is directed through a sample cavity with confocal or near confocal mirrors. The cavity is filled with a continuous flow of sample material. The output of the cavity is directed through an interference filter in one embodiment to define the spectral band. The output is then directed to a photomultiplier and amplifier circuit that is operatively connected to a plurality of counters, each of which is equipped with a logical gate input that allows counting of the pulses from the photomultiplier tube only when the gate is asserted. A further second plurality of counters is configured as a frequency divider chain that receives as input, a clock signal of at least three times the frequency at which the light is to be modulated. The output of this divider chain modulates the current driving the LED. The state of said second set of counters is logically decoded to generate non-overlapping logical waveforms such that one, and only one, is asserted at each instant in the cycle of modulation supplied to the LED; these non-overlapping waveforms constitute the gate inputs to said first plurality of counters. The use of the frequency divider chain overcomes the limitation of phase resolution of prior art lock-in amplifiers caused by their use of a phase lock loop to internally generate the two reference signals using one input. Alternatively, instead of measuring phase shift, the decay rate can be measured using appropriate measurement and analysis circuitry.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
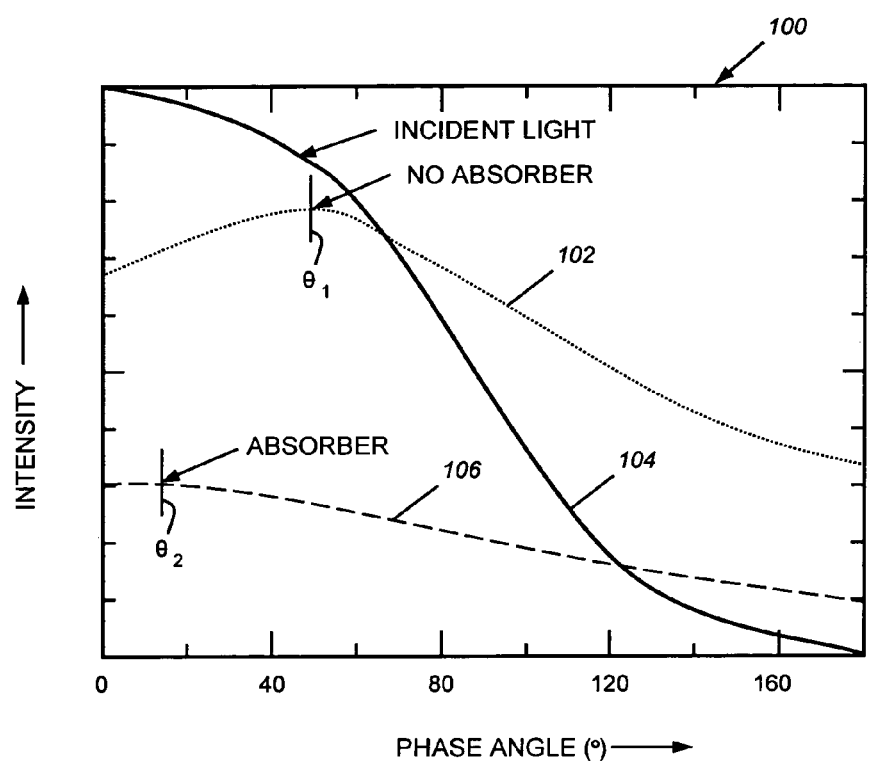
FIG. 1 is a graph of light intensity incident on a detector as a function of phase angle with respect to the modulation of the incident light in presence and absence of absorbing gas.
Figure 2:
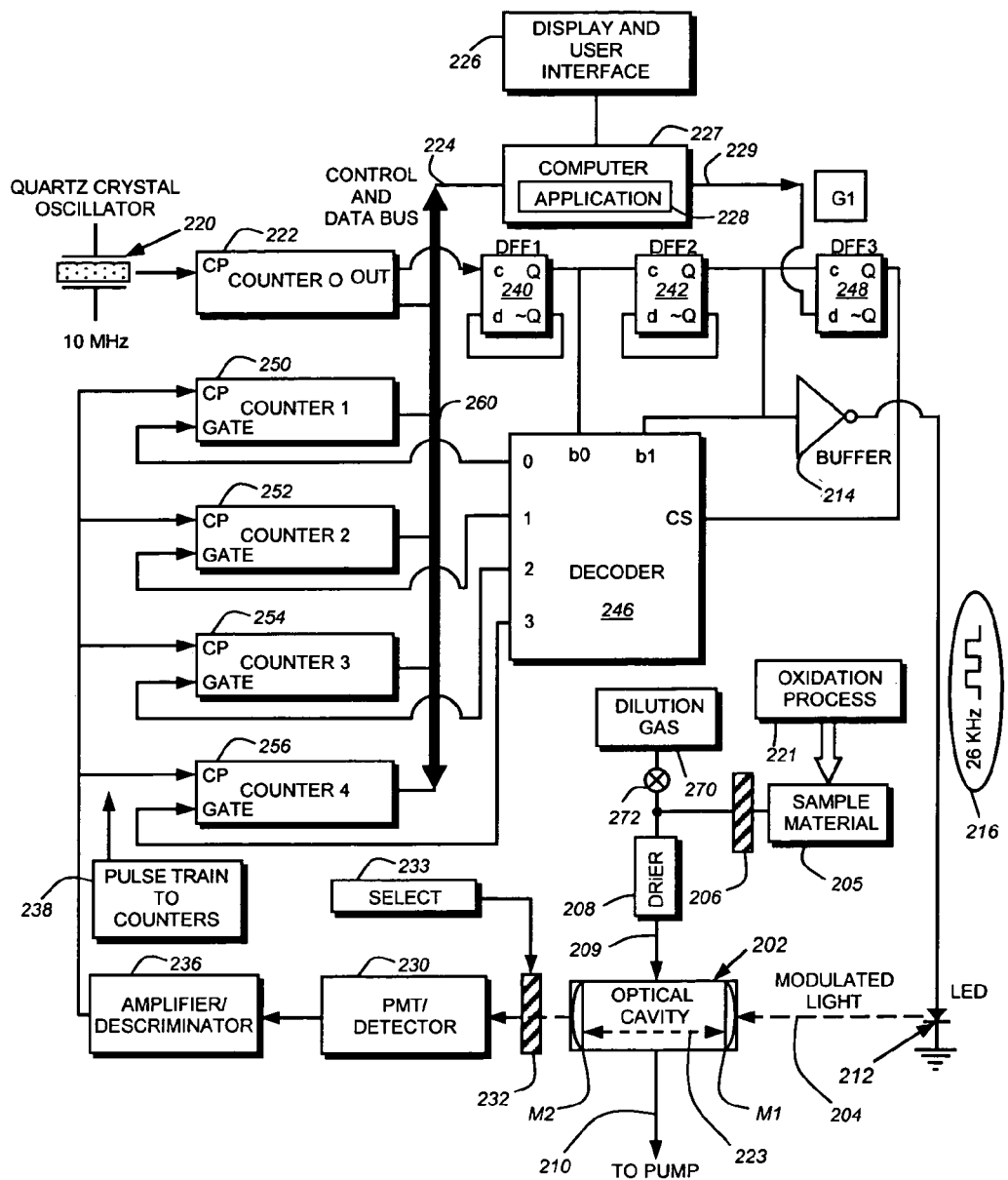
FIG. 2 is a block diagram of a system for performing cavity attenuated phase shift spectrographic analysis of a sample using incoherent light according to an embodiment of this invention.

FIG. 2 details a system 200 for detecting predetermined chemical species of a gaseous compound using a sample cavity 202 through which a modulated incoherent light 204 is passed and from which leaked light is analyzed for appropriate phase shift according to an illustrative embodiment of this invention. The sample is derived from an inlet that may communicate with the ambient environment, a sample container (or chemical-containing swab/strip) over which inert gas is passed or any other flowing gas source. In this embodiment, the gaseous sample material 205 is passed through a microparticulate filter 206 and moisture drier 208 of conventional design and whence into the cavity 202 via an inlet 209. An outlet 210 connected to a pump (not shown) may be used to draw gas at an appropriate flow rate through the cavity. It is noted that a variety of species can be detected in accordance with the teachings of this invention. In the example of FIG. 2, the detection of nitrogen dioxide ($NO_2$) is contemplated. In general, $NO_2$ can be derived by oxidizing various NO species. In the illustrative embodiment of FIG. 2, the sample containing NO species is flowed over a heated catalyst (for example) to convert the sample's NO species to $NO_2$ via oxidative processes. These oxidative processes are represented in FIG. 2 by the oxidation process box and arrow (221). In general, NO is not easily detected while $NO_2$ may be more readily detected using the techniques described herein. The chemical conversion to $NO_2$ according to this conventional approach is relatively complete, allowing an accurate concentration to be provided to the cavity. In alternate embodiments other oxidative processes may be employed, such as the treatment of the sample with a metered amount of ozone to thereby oxidize the NO-containing sample material.

As sample gas is continuously flowed through the cavity 202 it is exposed to a modulated light 204 from an LED 212 whereby absorption of the light can be detected and measured for either phase shift or decay. In particular, the LED 212 directs its modulated light 204 into the entrance mirror (M1) of the cavity 202. The LED 212 is driven by an amplified, buffered (buffer 214) modulated current 216 that is characterized by a square wave in this embodiment. The interconnection of the drive current 216 and the analysis circuit is described further below. The LED used in this embodiment is "blue" and operates in the approximate wavelength of 430 (±10) nm. Notably, this is the wavelength (420-440 nm) particularly suited to detect $NO_2$ while avoiding detection of virtually all other trace species. In particular, while the ozone Chappuis bands extend down to 440 nm, the ozone absorption coefficient at these wavelengths is on the order of $10^{-4}$ that of $NO_2$ (approximately 0.001 cm$^{-1}$ atm$^{-1}$). Only aromatic hydrocarbons with four or more rings exhibit absorption coefficients on the order of 500 cm$^{-1}$ atm$^{-1}$, which in turn implies that concentrations of such compounds would have to exceed several tens of parts per trillion to interfere with a typical sample measurement. This is unlikely except in the presence of significant quantities of such hydrocarbons (e.g. near a chemical plant where such compounds are present).

Figure 3:
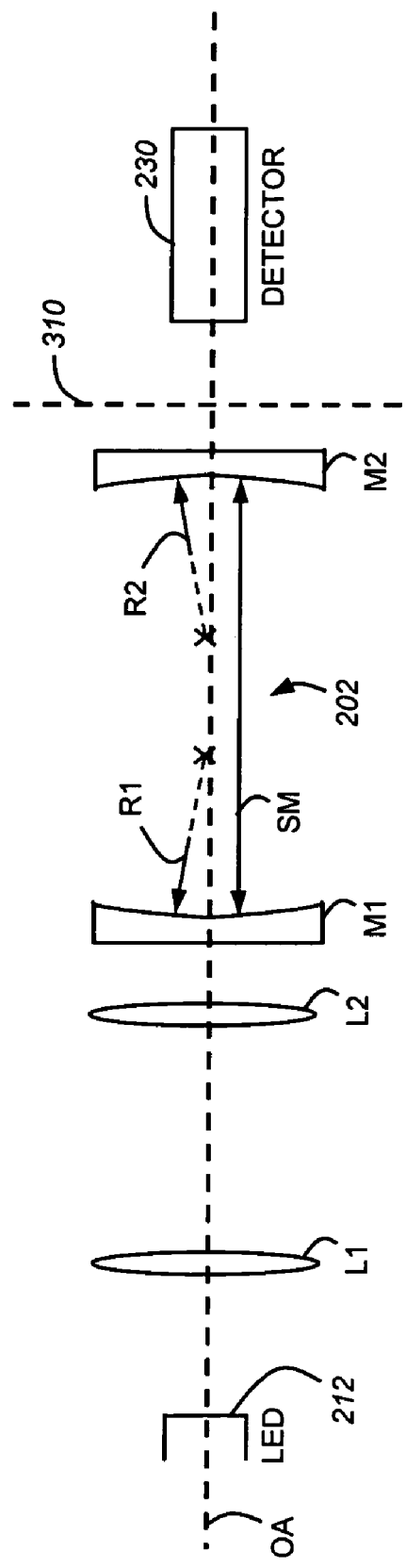
FIG. 3 is a more-detailed schematic cross section of the cavity and associated optics of FIG. 2.

With further reference to FIG. 3, the optics of the cavity 202 and associated transmission/detection optics is shown in further detail. In general, the cavity consists of two confocal or near-confocal mirrors M1 and M2. The reflectivity of the surface of each of the entrance and exit mirrors (M1 and M2, respectively) is 0.9995-0.9998 or more, allowing photons a substantial number of bounces (represented by double arrow 223 in FIG. 2), prior to leakage from the exit mirror M2.

In an exemplary embodiment, the respective radius of curvature R1 and R2 for each of the mirrors M1 and M2 is approximately 25 cm, and are spaced apart a distance SM of slightly less than 25 cm. In general, the optimum cavity geometry for use with an incoherent source is near-confocal, i.e. the radii of curvature of the mirrors are slightly longer or shorter than the mirror spacing. The general configuration of the cavity and the optical elements that couple light from the LED 212 into it as shown in FIG. 2. The lens L1 forms an image of the LED onto the entrance mirror, M1. The lens L2, including the effect of the curvature of M1, forms an image if the illuminated portion of L1 onto the exit mirror, M2. By suitable choice of the spacings and focal lengths of the lenses L1 and L2, these two images can be made the optimal size, which must be smaller than the mirror diameter to avoid spillover losses. Exactly how much smaller is a function of the mirror radius and spacing. (The mirrors are assumed to be identical.)

Once a photon has been transmitted through the entrance mirror's (M1) reflective coating into the cavity 202, it is reflected between the mirrors many times until it either escapes through one of the mirror coatings (M1 or M2) or is absorbed (or scattered) by the sample gas in the cavity. The optical elements and mirrors of the cavity are aligned along an optical axis depicted by the dashed line OA in this example. The path within the cavity is described by the set of discrete points at which a ray (i.e. the injected photon) strikes each mirror in turn. The properties of rays in a cavity of this kind are fundamental to the operation of most lasers, and have been studied in detail for many years. One result is the fact that the ray height (distance from the cavity axis at which the ray strikes a mirror) and slope vary sinusoidally with distance traveled (in units of the mirror spacing). The frequency of that sinusoidal motion is a function of the radii and spacings of the mirrors.

In general, at some points in its travel, the height of some of the rays in the cavity will be greater than the radius of the illuminated area of the mirrors. To avoid spillover losses, the illuminated area on the mirrors should be reduced, thereby reducing the area and solid angle within which the cell accepts light from the LED. In practice, the exactly confocal geometry may typically be impractical because small errors in radius that make the radii unequal cause the ray path to become unstable. This is avoided by making the radii R1 and R2 a few percent longer or shorter than the cavity spacing SM, a change that causes insignificant change in the light throughput.

Note that a series of optics depicted as dashed line is provided at the exit mirror M2 outlet to focus light on the detector 230. These optics can include an appropriate interference filter 232 (FIG. 2) that attenuates the bands of light presented to the detector 230 so that they more closely match those expected for the subject species. In one embodiment, the filter 232 can have a selectable wavelength, via a selection input (233), so as to detect on and off an absorption feature. In this manner the filter may allow for differential absorption measurement of the species in the sample.

With reference again to FIG. 2, the detector receives leaked photons from the exit mirror M2 of the cavity via the above-described interference filter 232. The detector 230 can be any acceptable photon-detection arrangement that converts received photons into electronic pulses. For example, a photomultiplier tube (PMT) may be employed in an illustrative embodiment. In a n alternate embodiment, however, a vacuum photodiode is employed. This form of detector comprises a photocathode and a collection electrode. Such devices possess large detection areas (1 cm diameter for example) eliminating the need for careful optical focusing of the signal beam into the detector. Such photodiode detectors also possess very low capacitance, which minimizes the contribution of voltage noise from the associated preamplifier as compared to a regular silicon photodiode which has relatively high capacitance and small area. These vacuum diodes require only modest bias voltages (typically 15V) and, although a somewhat more expensive than high-quality silicon photodiodes, are far less costly than photomultiplier tubes. They provide approximately 25% quantum efficiency.

The pulses generated by the detector are routed through an amplification and discrimination circuit 236 that can be of conventional design. This circuit provides the appropriate voltage level for the output pulse train 238 so that it can be employed by the phase shift analysis circuit described below. The circuit 236 can also filter unwanted noise and transients known to be outside the desired pulse bandwidth.

Where a photomultiplier tube (PMT) is employed as the detector 230, it is used at a gain of approximately $10^6$—i.e. for each photoelectron emitted from the PMT's cathode, a pulse containing $10^6$ electrons is delivered to the amplifier/discriminator 236. For each input pulse containing more than a preset number of electrons, the amplifier/discriminator emits a logic-level pulse of determinate duration (in this case, approximately 200 ns). These pulses are delivered to the clock inputs of Counters 1 through 4, which are described further below. In general, at any given time, the pulses are counted by only one of the counters to effect desired phase shift measurement In this embodiment, it is contemplated that the various electronic components described below may be implemented on a common hardware peripheral board and or chipset. This increases processing speed and reduces latency in signal transmission. In this embodiment, a central clock signal oscillator 220 is provided to drive both the LED (via a divide-by-N counter (Counter 0 (222)) and driving buffer 214) and to provide timing signals for the phase shift analysis circuit comprising four counters described below. In this embodiment, the peripheral board is connected by an appropriate data bus 224 to a general purpose computer 227 that can be any appropriate microcomputer having an operating system, a display and user interface 226. The computer 227 includes an application 228 that can interpret the phase shift data it receives from the board and provide an appropriate mathematical analysis so that species concentration can be computed. The computer 227 also provides control signals via the bus 229 to the phase shift analysis circuit as will be described further below. In general, this embodiment employs the computer's parallel port for communication with the peripheral board, but a variety of communication links can be employed in alternate embodiments.

According to prior art arrangements, phase shift measurements have relied on the use of quadrature lock-in amplifiers which are not sufficiently accurate at the modulation frequencies encountered in this type of device to provide high phase resolution. The use of a frequency divider chain starting from a single clock and generating both in-phase and quadrature reference signals overcomes the limitation of phase resolution associated with prior art lock-in amplifiers caused by their use of a phase lock loop (PLL) to internally generate the two reference signals using one input.

Alternatively, prior art pertaining to detection of signal time decay relies on high-speed sampling of the decaying signal followed by conversion to a digital signal. This technique requires the use of expensive, high-speed sampling and digitizing circuitry. Whereas, the alternative approach described herein is to divide each modulation cycle of the light source into a finite number of equal consecutive windows and then integrate the light signal recorded during each of those windows. These windows are likewise generated by division from a single frequency source. Since the decay is known to be exponential to a very high degree of approximation, a fairly limited number of windows can be used to accurately reconstruct the decay curve.

Referring again to the circuit 100 of FIG. 2 analysis of phase shift is accomplished by the computer application based on the readout of four programmable counters that are collectively part of the phase shift analysis circuit according to this embodiment, labeled Counter 1 through Counter 4. (Note: Counter 0 is used to generate the system timing signals as described above and further below.) In this embodiment, the counters are type 82C54, the use of which is well known in the art. These counters are controlled and read out over the data bus connected to the computer 227.

In the illustrative embodiment, Counter 0 (222) receives at its clock pulse input (denoted CP) the logic-level output of a 10 MHz oscillator 220. The precise frequency of CP is preselected. Counter 0 is programmed to divide this 10 MHz input train by an integer, (96 in this example), to produce a pulse train at its output (at a frequency of approximately 104 KHz in this case). This pulse train drives the clock input of D-flipflop DFF1 (240), which, with DFF2 (242), is configured to further divide the frequency by 4 (to approximately 26 KHz). The output of DFF2 is a square wave that (through the buffer amplifier 214) drives the LED at a frequency of approximately 26 KHz.

Figure 4:
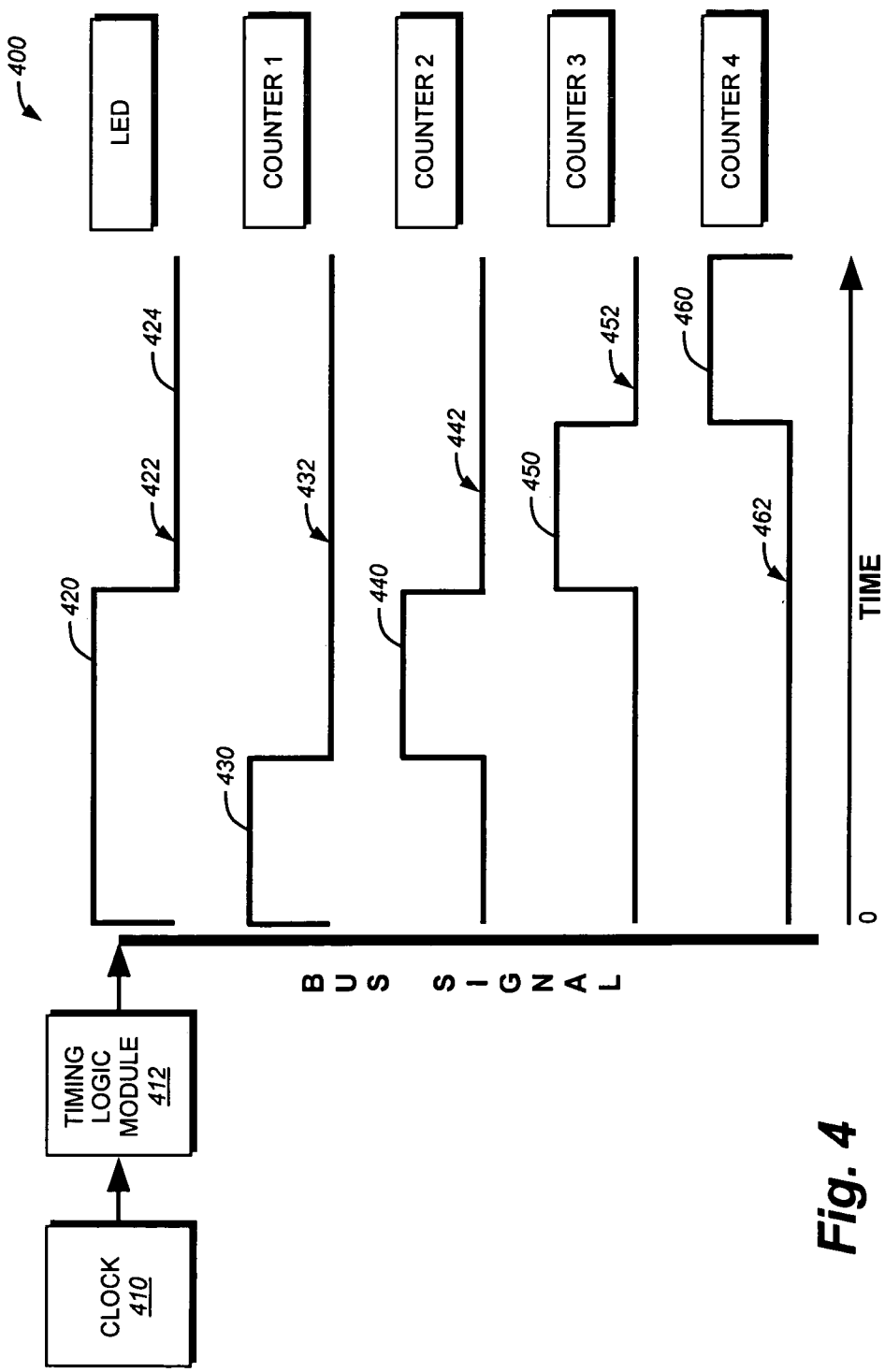
FIG. 4 is a timing diagram schematically detailing the timing of signals with respect to the LED and each signal analysis counter in the system of FIG. 1.

The outputs of DFF1 and DFF2 also supply bits 0 and 1 respectively to a binary-to-one-of-four decoder 246. Thus, each of the four outputs of the decoder is in turn high for 25% of the modulation cycle of the light output of the LED. Each decoder output controls the gate input of one of the other counters (Counter 1 through Counter 4—250, 252, 254 and 256, respectively), which only count the pulses received by their clock inputs ("CP") when the gate input ("gate") is high Referring briefly to FIG. 4, the timing of the signals generated by the LED circuit (Counter 0 in conjunction with the D-flipflops, DFF1 and DFF2) versus each of Counters 1-4 are shown in the simplified timing diagram 400. These each translate into a discrete signal provided to the bus 260 for transmission to the gate inputs of counters 1-4. The clock signal generated by the oscillator 220 is referenced generally as "CLOCK" 410 and the overall timing logic, (consisting in FIG. 2 of DFF1 (240), DFF2 (242), decoder 246. As shown, for each high cycle 420 by the LED/Counter 0 signal 422, the Counter 1 signal 432 is high (430) only for the first half and the Counter 2 signal 442 is high (440) only for the second half. Likewise, for each low cycle 424 of LED/Counter 1, the signal 432 of Counter 1 and the signal 442 of Counter 2 remain low, and the signal 452 of Counter 3 remains high (450) for only the first half of the Counter 0 low cycle 424. Likewise, the signal 462 of Counter 4 remains high (460) for only the second half of Counter 0's low cycle 424.

To control the counting process, the computer supplies logic level signal G1 to the data input of DFF3 (248), which gets as its clock input "c" the output "Q" of DFF2. The output of DFF3 goes to the chip-select input (CS) of the Decoder. When that input (from the DFF3) to the decoder 246 is low, all the output lines from the decoder 246 are held low, and thus none of the counters is actively counting. At that time, the accumulated counts are stable, and can be read out over the data and control bus.

Since the signal at CS is the output of DFF3, it can only change state on the leading edge of transitions of DFF2 (242), and thus during any observation, the four counters (Counters 1-4) will have been enabled for the same total duration. As the computer application 228 reads the relative number of detected photons in each of the time windows defined by the gate inputs to the counters, an accurate measurement of phase shift may be obtained. This phase shift is correlated with an absorber concentration and the resulting concentration may be continuously reported by the display 226 in any appropriate format (e.g. graphical, alpha-numerical, etc.).

In summary, the use of a spectrally and spatially incoherent light source, such as the above-described LED, eliminates many of the difficulties associated with laser-based cavity ringdown techniques. It guarantees that all axial and transverse modes of the cavity are equally excited. Furthermore, in the example of a continuous absorber (such as a halogen gas) or a quasi-continuous absorber (such as nitrogen dioxide), the need to account for the spectral distribution of the cavity modes is eliminated because the absorber lacks substantially resolved spectral lines. According to the teachings of this invention, the change in phase shift or decay rate (or ringdown time) for a given concentration of absorber does not vary with changes in cavity length on the order of a wavelength of the light used, a problem which must be confronted when using lasers to detect species which exhibit line structure.

Nitrogen dioxide, chlorine, bromine, iodine and chlorine dioxide are all gases that possess comparatively structureless absorption bands in the visible and near-visible region of the electromagnetic spectrum. Suitable LEDs are also readily available for their detection. LEDs of a wavelength suitable for the detection of fluorine, ozone and sulfur dioxide in the ultraviolet are available experimentally and commercially available versions are in current development.

According to alternate embodiments, the system can be adapted to measure the following species (among others) by employing an LED operating generally within the accompanying wavelengths:

| nitrogen dioxide | 350-500 nm |
| fluorine | 220-360 nm |

-continued

| | |
|---|---|
| chlorine | 270-420 nm |
| bromine | 350-550 nm |
| iodine | 420-620 nm |
| ozone | 200-300 nm |
| sulfur dioxide | 200-300 nm |
| chlorine dioxide | 300-450 nm |
| aromatic species | 200-500 nm |

(wherein aromatic species are defined to include, but are not limited to, benzene, toluene, naphthalene, pyrene, dioxins, etc.)

Note further that a resonant cavity of particular length and reflectivity can be used to detect a limited range of species concentration because of the effects of the Beer-Lambert Law—i.e., increases in species concentration produce smaller and smaller changes in the observed absorption. When this saturation effect occurs, this problem can be overcome by diluting the sample by a known amount of air or a non absorbing/non-reactive gas (dilution gas 270 controlled by valve 272 in FIG. 2) in order to cause its absorption to stay within the optimum range of the cavity.

According to an alternate embodiment, an improved system for detecting species would include the ability to provide a true differential absorption measurement which requires measurement at two different wavelength regions, one at which the species of interest absorbs the radiation and the other where it is more transparent. Examples of means to provide selective filters are: dielectric coated interferences filters, Lyot filters, or a non-dispersive gas cell arrangement. To this end, a measurement of total atmospheric extinction by the system can be made by measuring one or more wavelengths. In accomplishing the measurement of total atmospheric extinction caused solely by particulate matter, the system subtracts the results obtained by filtering the measured air so as to remove all particulates above a predetermined size using the filter 206.

Finally, according to an embodiment of this invention, one application of great interest is the detection of explosive materials. In one implementation, an explosive material which contains nitrogen and oxygen as part of its constituents is thermally heated or otherwise caused to decompose. As such, the nitrogen dioxide gas that is normally evolved can be sensitively detected using this technique by thereafter directing it through the cavity and reading the concentration of nitrogen dioxide as described generally above.

The foregoing has been a detailed description of illustrative embodiments of this invention. Various modifications and additions can be made without departing from the spirit and scope thereof. For example, while an LED is employed as an incoherent light source, it is contemplated that other types of equivalent light sources with sufficient intensity and modulation speed can be substituted if and when available. As such the term LED as used herein should be taken broadly to include other types of light sources that provide similar or appropriate levels of performance. In addition the level of output intensity of the light source is variable and an appropriate detector and amplifier can be adapted to operate with the chosen intensity. In addition, it is expressly contemplated that the counter-based phase shift analysis or measurement circuit described herein can be replaced with other circuits that allow measurement of phase shift or decay rate within acceptable accuracy and speed parameters to provide real-time or near-real-time concentration measurement in a flow of gas containing a species of interest.

Likewise, appropriate optical filters and multiple light sources can be used to measure multiple species where desirable. Accordingly, this description is meant to be taken only by way of example, and not to otherwise limit the scope of this invention.

What is claimed is:

1. A system for detecting a gaseous species comprising:
   a modulated light emitting diode (LED);
   a resonant optical cavity having a cavity area for receiving the gaseous species and into which the LED emits light;
   an optical detector receiving leaked light from the optical cavity; and
   a measurement process operatively connected to an output of the detector that measures at least one of a phase shift or a decay rate of the leaked light to thereby derive a concentration of the species in the cavity wherein the measurement process is configured to perform synchronous detection by using frequency divided signals from a single clock source that both drive the LED and provide reference signals used in reading the output of the detector.

2. The system as set forth in claim 1 wherein the cavity includes a pair of opposing confocal or near-confocal mirrors.

3. The system as set forth in claim 2 further comprising an optical interference filter located between the cavity and the detector that limits a spectral band of the leaked light.

4. The system as set forth in claim 2 further comprising a selectable wavelength filter located between the cavity and the detector that allows on and off detection of an absorption feature of the species for differential absorption measurement of the species.

5. The system as set forth in claim 2 wherein the LED and the cavity are configured so as to select at least one of the following species at the accompanying wavelength:

| | |
|---|---|
| nitrogen dioxide | 350-500 nm; |
| fluorine | 220-360 nm; |
| chlorine | 270-420 nm; |
| bromine | 350-550 nm; |
| iodine | 420-620 nm; |
| ozone | 200-300 nm; |
| sulfur dioxide | 200-300 nm; |
| chlorine dioxide | 300-450 nm; and |
| aromatic species | 200-500 nm. |

6. The system as set forth in claim 3 wherein the LED and the cavity are configured so as to select at least one of the following species at the accompanying wavelength:

| | |
|---|---|
| nitrogen dioxide | 350-500 nm; |
| fluorine | 220-360 nm; |
| chlorine | 270-420 nm; |
| bromine | 350-550 nm; |
| iodine | 420-620 nm; |
| ozone | 200-300 nm; |
| sulfur dioxide | 200-300 nm; |
| chlorine dioxide | 300-450 nm; and |
| aromatic species | 200-500 nm. |

7. The system as set forth in claim 4 wherein the LED and the cavity are configured so as to select at least one of the following species at the accompanying wavelength:

| | |
|---|---|
| nitrogen dioxide | 350-500 nm; |
| fluorine | 220-360 nm; |
| chlorine | 270-420 nm; |
| bromine | 350-550 nm; |
| iodine | 420-620 nm; |
| ozone | 200-300 nm; |
| sulfur dioxide | 200-300 nm; |
| chlorine dioxide | 300-450 nm; and |
| aromatic species | 200-500 nm. |

8. The system as set forth in claim 2 wherein nitrogen dioxide is the species and is converted from a nitrogen monoxide species by oxidation prior to being received by the cavity.

9. The system as set forth in claim 2 wherein the gaseous species is diluted by a know amount of a non-absorbing and non-reactive gas prior to being received by the cavity whereby an effective concentration measurement range is extended.

10. The system as set forth in claim 2 wherein the gaseous species is derived from a sample suspected of including explosive compounds in which the species is released from the sample by heating the sample.

11. The system as set forth in claim 2 wherein the measurement process is configured to measure total atmospheric extinction at one or more wavelengths.

12. The system as set forth in claim 11 wherein the measurement process is configured to measure total atmospheric extinction caused solely by particulate matter by subtracting from total extinction measurements results obtained by filtering measured sample gas so as to remove all particulate matter above a predetermined size.

13. A system for detecting gaseous species comprising:
a modulated light source;
a resonant optical cavity receiving light emitted from the modulated light source;
an optical detector receiving leaked light from the cavity; and
a measurement process configured to measure one of either a decay rate of a signal transmitted from the optical detector or a phase shift of the signal transmitted from the detector, the process being further configured to perform synchronous detection by using frequency divided signals from a single clock source that both drive the modulated light source and provide reference signals used in reading the output of the detector.

14. The system as set forth in claim 13 wherein the cavity includes entrance and exit mirrors arranges in a confocal or near-confocal configuration.

15. The system as set forth in claim 14 wherein the modulated light source comprises an LED.

16. A method for detecting a gaseous species comprising:
providing a modulated light emitting diode (LED);
emitting light from the LED into a resonant optical cavity and receiving the gaseous species in the cavity;
receiving, with an optical detector, leaked light from the optical cavity;
generating signals having a frequency derived from a single clock source by dividing a clock source frequency by an integer;
using the signals to both drive the LED and to provide reference for reading an output of the detector; and
measuring the output of the detector so as to measure at least one of a phase shift or a decay rate of the leaked light and thereby deriving a concentration of the species in the cavity.

17. A system for detecting a gaseous species comprising:
a square-wave modulated light source;
a resonant optical cavity including a pair of opposing confocal or near-confocal mirrors, having a cavity area for receiving the gaseous species and into which the light source emits light;
an optical detector receiving leaked light from the optical cavity,
a measurement process operatively connected to an output of the detector to measure the phase shift or intensity of the leaked light to derive a concentration of the species in the cavity, wherein the measurement process is configured to perform synchronous detection by providing a signal to drive the light source and further providing in-phase and quadrature reference signals used in synchronously demodulating the output of the detector, wherein the signals have a frequency derived from a single clock source by dividing the clock source's frequency by an integer.

18. The system as set forth in claim 17 further comprising an optical interference filter located between the cavity and the detector to limit a spectral band of the leaked light.

19. The system as set forth in claim 17 further comprising a selectable wavelength filter located between the cavity and the detector that allows on and off detection of an absorption feature of the species for differential absorption measurement of the species.

20. The system as set forth in claim 17 wherein the LED and the cavity are configured to select at least one of the following species at the accompanying wavelength:

| | |
|---|---|
| nitrogen dioxide | 350-500 nm; |
| fluorine | 220-360 nm; |
| chlorine | 270-420 nm; |
| bromine | 350-550 nm; |
| iodine | 420-620 nm; |
| ozone | 200-300 nm; |
| sulfur dioxide | 200-300 nm; |
| chlorine dioxide | 300-450 nm; and |
| aromatic species | 200-500 nm. |

21. The system as set forth in claim 17 wherein nitrogen dioxide is the species and is converted from a nitrogen monoxide species by oxidation prior to being received by the cavity.

22. The system as set forth in claim 17 wherein the species is diluted by a know amount of a non-absorbing and non-reactive gas prior to being received by the cavity, to extend an effective concentration measurement range.

23. The system as set forth in claim 17 wherein the species is derived from a sample suspected of including explosive compounds in which the species is released from the sample by heating the sample.

24. The system as set forth in claim 17 wherein the measurement process is configured to measure total atmospheric extinction at one or more wavelengths.

25. The system as set forth in claim 24 wherein the measurement process is configured to measure total atmospheric extinction caused solely by particulate matter by subtracting from total extinction measurements results obtained by filtering measured sample gas so as to remove all particulate matter above a predetermined size.

* * * * *